United States Patent [19]

Jolly et al.

[11] 4,207,240
[45] Jun. 10, 1980

[54] 4,5-SECO-ESTRANE-3,5,17-TRIONE DERIVATIVES

[75] Inventors: Jean Jolly, Fontenay-sous-Bois; Bernard Matra, Aulnay-sous-Bois; Primo Rizzi, Villemomble, all of France

[73] Assignee: Roussel Uclaf, Paris, France

[21] Appl. No.: 15,470

[22] Filed: Feb. 26, 1979

[30] Foreign Application Priority Data

Mar. 6, 1978 [FR] France .................. 78 06307

[51] Int. Cl.² ........................... C07D 317/10
[52] U.S. Cl. .................. 260/340.9 AS; 260/340.7; 260/397.4; 568/373
[58] Field of Search ................. 260/340.9 AS

[56] References Cited
U.S. PATENT DOCUMENTS 3,980,687  9/1976  Warnant et al. ........... 260/340.9 AS Primary Examiner—Ethel G. Love Attorney, Agent, or Firm—Hammond & Littell, Weissenberger and Muserlian

[57] ABSTRACT

Novel 4,5-seco-estrane-3,5,17-trione derivatives of the formula

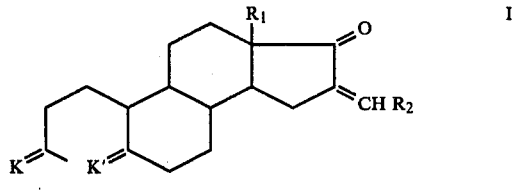

wherein $R_1$ is alkyl of 1 to 3 carbon atoms, $R_2$ is selected from the group consisting of hydrogen and alkyl of 1 to 5 carbon atoms and K and K' are individually blocked ketones in the form of ketals which are intermediates for the preparation of therapeutically active steroids and their preparation and novel intermediates.

8 Claims, No Drawings

4,5-SECO-ESTRANE-3,5,17-TRIONE DERIVATIVES

STATE OF THE ART

Compounds of the formula

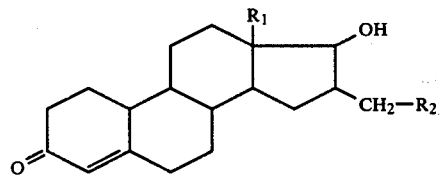

wherein $R_1$ and $R_2$ have the above definition are known compounds described by Kingl et al [Steroids, 1959, p. 595] and U.S. Pat. No. 3,856,829 and are known to have interesting pharmacological properties. For example, 16β-ethyl-Δ⁴-estrene-17β-ol-3-one has a very interesting antiandrogenic activity and is useful for the treatment of adenome of the prostate. However, until now, the products of formula V could only be produced by a long and industrially difficult process of nine steps starting from oestrone as described in U.S. Pat. No. 3,856,829, French Pat. No. 4957M, Z Physiol. Chem., Vol. 208 (1932) p. 127 and J. Chem. Soc., 1938, p. 1997.

OBJECTS OF THE INVENTION

It is an object of the invention to provide the novel intermediates of formula I and to provide a novel process and novel intermediates for their preparation.

It is another object of the invention to provide a novel economical process for the preparation of compounds of formula V.

These and other objects and advantages of the invention will become obvious from the following detailed description.

THE INVENTION

The novel 4,5-seco-estrane-3,5,17-trione derivatives of the invention have the formula

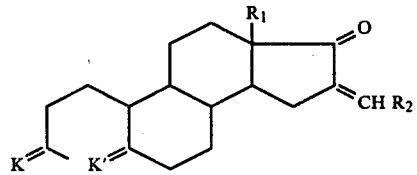

wherein $R_1$ is alkyl of 1 to 3 carbon atoms, $R_2$ is selected from the group consisting of hydrogen and alkyl of 1 to 5 carbon atoms and K and K' are individually blocked ketones in the form of ketals.

Preferably, $R_1$ is methyl or ethyl but may be propyl or isopropyl. Examples of $R_2$ as alkyl of 1 to 5 carbon atoms are methyl, ethyl, n-propyl, isopropyl, n-butyl, isobutyl, tert.-butyl or pentyl. Examples of ketals of K and K' are cyclicalkyl ketals of 2 to 4 carbon atoms such as ethyleneketal or propyleneketal or dialkylketals with alkyls of 1 to 4 carbon atoms such as dimethylketal or diethylketal.

Among the preferred compounds of formula I are those wherein $R_1$ is methyl, those wherein $R_2$ is methyl and those wherein K and K' are a 1,2-ethanediyl cyclicacetal. Particularly preferred is 3,5-bis-(1,2-ethyleneketal)-16-ethylidene-4,5-seco-estrane-3,5,17-trione.

The novel process of the invention for the preparation of the compounds of formula I comprises reacting in the presence of a base a compound of the formula

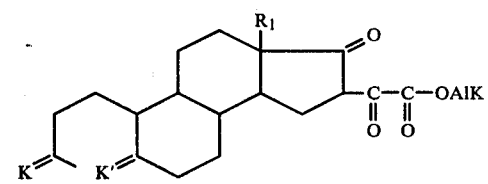

wherein K, K' and $R_1$ have the above definitions and AlK is alkyl of 1 to 8 carbon atoms or an alkali metal enolate of the formula

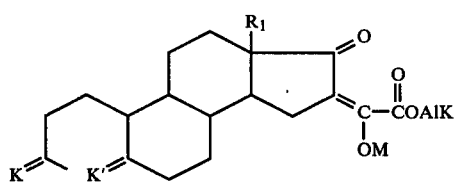

wherein K, K', $R_1$ and AlK have the above definitions and M is an alkali metal with an aldehyde of the formula

wherein $R_2$ has the above definition to obtain a compound of formula I.

In a preferred mode of the process, the alkali metal of M is sodium or potassium and AlK is methyl or ethyl. The base for the condensation is preferably sodium hydroxide or potassium hydroxide, an alkali metal carbonate such as potassium carbonate or a tertiary amine such as triethylamine.

The compounds of formulae II$_a$ and II$_b$ are novel intermediates and particularly preferred is 3,5-bis-(1,2-ethyleneketal)-16-β-ethyl acetate-4,5-seco-estrane-3,5,17,α-tetraone.

The novel process of the invention for the preparation of the compounds of formulae II$_a$ and II$_b$ comprises reacting a dialkyl oxalate of the formula

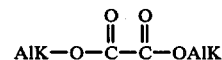

wherein AlK has the above definition with a compound of the formula

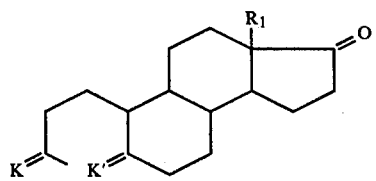

wherein K, K' and $R_1$ have the above definition in the presence of an alkali metal base to obtain the compound of formula II$_b$ which may be isolated, if desired, or reacted with an acid agent to obtain the compound of formula II$_a$.

In a preferred mode of the process, the alkali metal base is sodium hydroxide or potassium hydroxide or an alkali metal alcoholate such as sodium methylate or sodium hydride. The acid agents are preferably hydrochloric acid or acetic acid. The compounds of formula III are known and may be made by the process of French Pat. No. 1,490,590, for example.

The novel process of the invention for the preparation of a compound of formula V comprises reacting a compound of formula I with an hydrogenation agent capable of saturating the double bond in the 16 position to obtain a compound of the formula

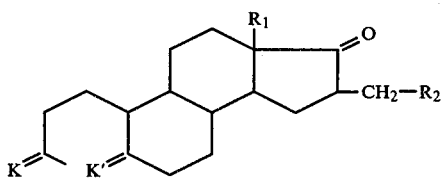

reacting the latter with a reducing agent to reduce the 17-keto group and then an acid hydrolysis agent to obtain a compound of the formula

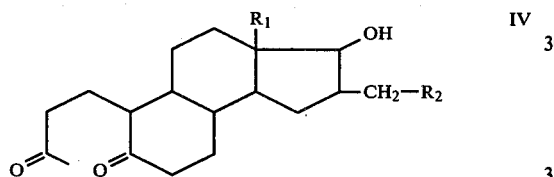

and reacting the latter with a basic agent to obtain a compound of formula V.

In a preferred mode of the process, R$_2$ is methyl and more preferably 3,5-bis-(1,2-ethyleneketal)-16-ethylidene-4,5-seco-estrane-3,5,17-trione is used to prepare 16β-ethyl-Δ$^4$-estrene-17β-ol-3-one. The preferred hydrogenation agent is hydrogen in the presence of a palladium catalyst and the preferred reducing agent is sodium borohydride or lithium aluminum hydride. The acid hydrolysis agent is preferably hydrochloric acid, sulfuric acid, acetic acid, citric acid or p-toluene sulfonic acid. The basic cyclization agent to form ring A is preferably an alkali metal alcoholate such as sodium methylate, sodium ethylate, sodium tert.-butylate, potassium tert.-butylate or potassium tert.-amylate or an alkali metal base such as sodium hydroxide or potassium hydroxide.

The compounds of formula I and their preparation from the compounds of formulae II$_a$ or II$_b$ is original and not suggested by the state of the art. The compounds of formula I are of great industrial interest as they permit access to the compounds of formula V in 5 steps starting from compounds of formula III in a simple and industrially easy process. The compounds of formula III can be easily prepared by a total synthesis and they have been produced industrially for a period of time as they are intermediates in the synthesis of very many 19—nor steroids which are sold in large quantities throughout the world.

In the following examples there are described several preferred embodiments to illustrate the invention. However, it should be understood that the invention is not intended to be limited to the specific embodiments.

EXAMPLE 1

3,5-bis-(1,2-ethyleneketal)-16-ethylidene-4,5-seco-estrane-3,5,17-trione

STEP A: 3,5-bis-(1,2-ethyleneketal)-16β-ethyl acetate-4,5-seco-estrane-3,5,17,α-tetraone 66 g of sodium methylate were added at −10° C. to a solution of 200 g of 3,5-bis-(1,2-ethyleneketal)-4,5-seco-estrane-3,5,17-trione (process of French Pat. No. 1,490,590) in 600 ml of dimethylformamide and then 160 ml of diethyl oxalate were added thereto at 0°±2° C. The mixture was stirred for 2 hours at 0° to 5° C. and then 100 ml of acetic acid were added thereto. Crystallization was induced by scratching in a mixture of 50—50 ice-water. The mixture was vacuum filtered and the recovered product was washed with water and dried to obtain 242.5 g of 3,5-bis-(1,2-ethyleneketal)-16β-ethyl acetate-4,5-seco-estrane-3,5,17,α-tetraone melting at about 100° C. which was used as is for the next step.

STEP B: 3,5-bis-(1,2-ethyleneketal)-16-ethylidene-4,5-seco-estrane-3,5,17-trione The product of Step A was added with stirring under nitrogen at 20° C. to 243 ml of anhydrous methanol and 121 g of potassium carbonate were added to the resulting suspension. The mixture was stirred at room temperature for 15 minutes and after cooling the mixture to −5°±2° C., 121 ml of acetaldehyde were added thereto. The mixture was stirred at 0° C. for 2 hours after which the temperature was allowed to rise to 20° C. The mixture was stirred at 20° C. for 16 hours and crystallization was induced by scratching in 182 g of mono-potassium phosphate and 730 ml of a 50—50 ice-water mixture. The mixture was vacuum filtered and the precipitate was washed with water and was dissolved in 1200 ml of methylene chloride. The aqueous phase was decanted and the organic phase was dried over magnesium sulfate and was vacuum filtered. The filter was rinsed with methylene chloride and 242 g of hydrated alumina was added to the filtrate over 20 minutes with stirring at 20°±2° C. The mixture was stirred for one hour and was vacuum filtered. The filter was rinsed with 240 ml of methylene chloride and the filtrate was evaporated to a volume of 240 ml. The solution was added with stirring to 1200 ml of refluxing isopropyl ether and the resulting solution was evaporated to a volume of 600 ml. The mixture was stirred at −10° C. for one hour and was then vacuum filtered. The recoverd product was rinsed with 120 ml of isopropyl ether and was dried to obtain 156.5 g of 3,5-bis-(1,2-ethyleneketal)-16-ethylidene-4,5-seco-estrane-3,5,17-trione melting at 131° C.

EXAMPLE 2

16β-ethyl-Δ$^4$-estrene-17β-ol-3-one

STEP A: 16β-ethyl-4,5-seco-estrane-17β-ol-3,5-dione

A current of hydrogen was passed through a mixture of 50 g of the product of Example 1, 0.4 ml of pyridine, 1,250 g of carbon activated with 10% palladium and 400 ml of methanol until 1700 ml of hydrogen were absorbed and dissolution was complete. The mixture was then stirred for 2 hours and was vacuum filtered to remove the catalyst. The filter was rinsed with methanol and the combined methanol phases contained 3,5-bis-(1,2-ethyleneketal)-16β-ethyl-4,5-seco-estrane-3,5,17 trione and 50 ml of water and 15 ml of N sodium hydroxide were added to 500 ml of the methanol solution. 2.45 g of sodium borohydride were added to the mixture over one hour and the mixture was stirred for 15 to 20 hours and was then reduced to a volume of 250 ml. 5 ml of acetic acid were slowly added with stirring at 20° C. to the mixture and the mixture was then stirred at 20° C. for 15 minutes. The resulting solution was slowly poured into 2500 ml of a 50—50 water-ice mixture and the mixture was stirred fo 30 minutes and was vacuum filtered. The recovered product was washed with water and was vacuum filtered again to obtain 107.5 g of 3,5-bis-(1,2-ethyleneketal)-16β-ethyl-4,5-seco-estrane-17β-ol 3,5 dione.

The said product was suspended in a solution of 150 ml of acetic acid and 93 ml of demineralized water and the suspension was heated at 40° C. with stirring for 2 hours. The mixture was cooled to 20° C. and was then poured into 1000 ml of a 50—50 water-ice mixture. The suspension was stirred for 30 minutes and was then vacuum filtered. The recovered product was washed with water and dried to obtain 34.4 g of raw product which was crystallized from toluene to obtain 29.340 g of 16β-ethyl-4,5-seco-estrane-17β-ol-3,5-dione, melting at 113° C.

STEP B: 16β-ethyl-Δ⁴-estrene-17β-ol-3-one

A suspension of 25 g of the product of Step A in 250 ml of methanol was heated to 50° C. with stirring and 9.4 ml of a solution of 400 g of sodium hydroxide per liter were added thereto. The solution was held at 50° C. for 30 minutes and then a mixture of 79 ml of water and 5.8 ml of a solution of 110% acetic acid were added thereto at 50° C. The suspension was cooled to 0° to 5° C. and was stirred for 30 minutes at 0° to 5° C. The mixture was vacuum filtered and the recovered product was washed with methanol and water and was then dried to obtain 21.4 g of raw product which was crystallized from ethyl acetate to obtain 19.800 g of 16β-ethyl-Δ⁴-estrene-17β-ol-3-one melting at 152°–153° C.

Various modifications of the products and processes of the invention may be made without departing from the spirit or scope thereof and it should be understood that the invention is intended to be limited only as defined in the appended claims.

We claim:

1. A compound of the formula

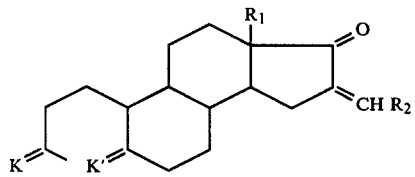

wherein $R_1$ is alkyl of 1 to 3 carbon atoms, $R_2$ is selected from the group consisting of hydrogen and alkyl of 1 to 5 carbon atoms and K and K' are individually blocked ketones in the form of ketals.

2. A compound of claim 1 wherein $R_1$ is methyl.

3. A compound of claim 1 wherein $R_2$ is methyl.

4. A compound of claim 1 wherein K and K' are both ethyleneketal.

5. A compound of claim 1 which is 3,5-bis-(1,2-ethyleneketal)-16-ethylidene-4,5-seco-estrane-3,5,17-trione.

6. A process for the preparation of a compound of claim 1 comprising reacting in the presence of a base a compound of the formula

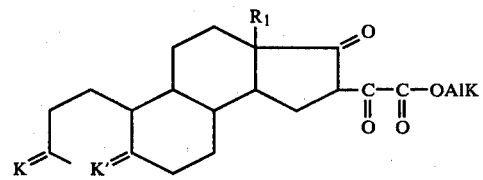

wherein K, K' and $R_1$ have the above definitions and AlK is alkyl of 1 to 8 carbon atoms or an alkali metal enolate of the formula

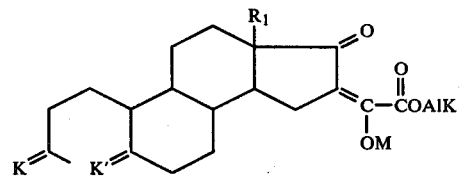

wherein K, K', $R_1$ and AlK have the above definition and M is an alkali metal with an aldehyde of the formula

wherein $R_2$ has the above definition to obtain a compound of claim 1.

7. A compound having a formula selected from the group consisting of

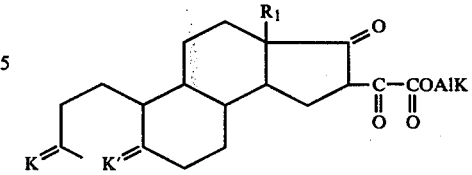

and

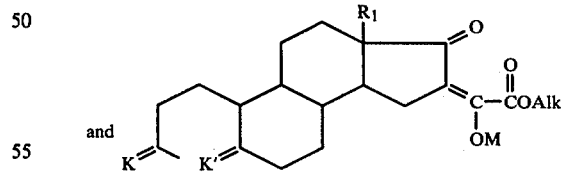

wherein $R_1$ is alkyl of 1 to 3 carbon atoms, AlK is alkyl of 1 to 8 carbon atoms, M is an alkali metal and K and K' are individually blocked ketones in the form of ketals.

8. A compound of claim 7 which is 3,5-bis-(1,2-ethyleneketal)-16β-ethyl-acetate-4,5-seco-estrane-3,5,17,α-tetraone.

* * * * *